United States Patent
Anderson et al.

(10) Patent No.: US 6,352,515 B1
(45) Date of Patent: Mar. 5, 2002

(54) NITI ALLOYED GUIDEWIRES

(75) Inventors: David M. Anderson, Temecula; Wayne E. Cornish, Fallbrook; Marc Mehrzad Jalisi; Nancy Nicotra, both of Temecula; Mark T. Richardson, Escondido, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/459,814

(22) Filed: Dec. 13, 1999

(51) Int. Cl.$^7$ .................................. A61B 5/00
(52) U.S. Cl. ........................... 600/585; 604/523
(58) Field of Search .................... 600/585; 604/523, 604/525, 528, 530

(56) References Cited

U.S. PATENT DOCUMENTS

| | | | |
|---|---|---|---|
| 4,538,622 A | 9/1985 | Samson et al. | 128/772 |
| 4,748,986 A | 6/1988 | Morrison et al. | 128/772 |
| 5,135,503 A | 8/1992 | Abrams | 604/164 |
| 5,341,818 A | 8/1994 | Abrams et al. | 128/772 |
| 5,345,945 A | 9/1994 | Hodgson et al. | 128/772 |
| 5,411,476 A | 5/1995 | Abrams et al. | 604/95 |
| 5,720,300 A | 2/1998 | Fagan et al. | 128/772 |
| 5,833,631 A | * 11/1998 | Nguyen | 600/585 |
| 5,885,381 A | 3/1999 | Mitose et al. | 148/564 |
| 5,951,793 A | 9/1999 | Mitose et al. | 148/563 |

FOREIGN PATENT DOCUMENTS

EP 0 873 734 A2 10/1998

OTHER PUBLICATIONS

U.S. Department of Commerce National Technical Information Service, *Effects of Alloying Upon Certain Properties of 55.1 Nitinol*, May 28, 1965.

* cited by examiner

Primary Examiner—John P. Lacyk
Assistant Examiner—Pamela L. Wingood
(74) Attorney, Agent, or Firm—Fulwider Patton Lee & Utecht, LLP

(57) ABSTRACT

The present invention is directed to an intracorporeal device, preferably a guidewire, and method for making the same. The device, has proximal and distal ends and includes an elongated high strength proximal portion having proximal and distal ends. The device further includes a distal portion having proximal and distal ends. The distal end of the proximal portion and the proximal end of the distal portion are connected by a connector. The distal portion is formed of a superelastic alloy composition. Preferably, the connector is also formed of the superelastic alloy composition. The superelastic alloy composition includes, in atomic percent, from about 28 to about 52% nickel, from about 48 to about 52% titanium, and up to about 20% of at least one alloying element selected from the group consisting of palladium, chromium, and hafnium.

21 Claims, 1 Drawing Sheet

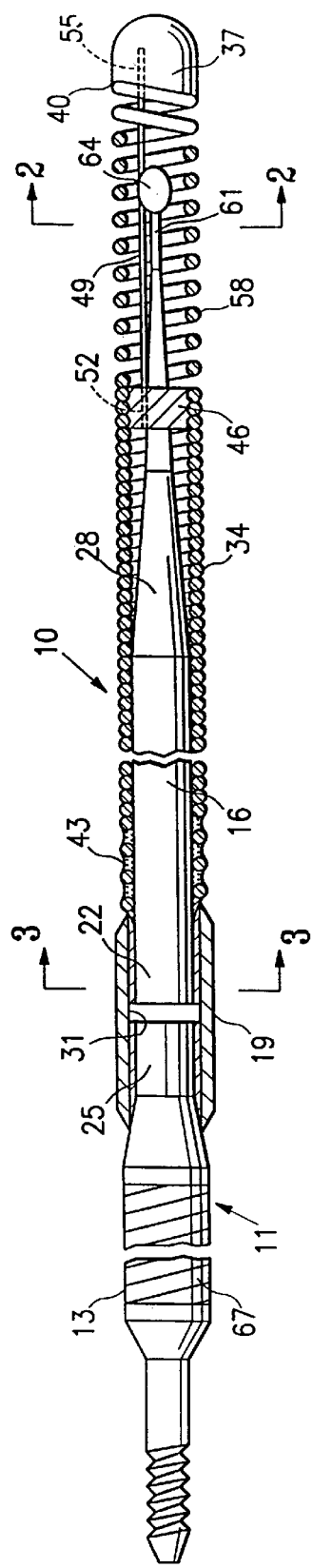
FIG. 1
FIG. 2
FIG. 3

NITI ALLOYED GUIDEWIRES

FIELD OF INVENTION

This invention relates to the field of guidewires for advancing intraluminal devices such as stent delivery catheters, balloon dilatation catheters, atherectomy catheters and the like within body lumens.

BACKGROUND OF THE INVENTION

Conventional guidewires for angioplasty and other vascular procedures usually comprise an elongated core member with one or more tapered sections near the distal end thereof and a flexible body such as a helical coil disposed about the distal portion of the core member. A shapeable member, which may be the distal extremity of the core member or a separate shaping ribbon which is secured to the distal extremity of the core member extends through the flexible body and is secured to a rounded plug at the distal end of the flexible body. Torquing means are provided on the proximal end of the core member to rotate, and thereby steer, the guidewire while it is being advanced through a patient's vascular system.

In a typical coronary procedure, a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the procedure is performed.

A requirement for guidewires is that they have sufficient column strength to be pushed through a patient's vascular system or other body lumen without kinking. However, guidewires must also be flexible enough to avoid damaging the blood vessel or other body lumen through which they are advanced. Efforts have been made to improve both the strength and flexibility of guidewires to make them more suitable for their intended uses, but these two properties are for the most part, diametrically opposed to one another in that an increase in one usually involves a decrease in the other.

Further details of guidewires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); and U.S. Pat. No. 5,345,945 (Hodgson et al.); all of which are incorporated herein in their entirety by reference.

Some guidewires have been formed from a pseudoelastic alloy such as a NITINOL (nickel-titanium or NiTi) alloy, to achieve both flexibility and strength. When stress is applied to NITINOL alloy exhibiting pseudoelastic characteristics at a temperature at or above which the transformation of martensite phase to the austenite phase is complete, the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation.

If the load on the specimen is removed before any permanent deformation has occurred, the martensitic phase of the specimen will elastically recover and transform back to the austenite phase. The reduction in stress first causes a decrease in strain. As stress reduction reaches the level at which the martensite phase transforms back into the austenite phase, the stress level in the specimen will remain essentially constant until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as pseudoelasticity. These properties to a large degree allow a guidewire core of a pseudoelastic material to have both flexibility and strength.

While the properties of the guidewire formed of the superelastic material were very advantageous, it was found that the guidewires and guiding members formed of materials having superelastic characteristics did not have optimum push and torque characteristics.

SUMMARY OF THE INVENTION

The present invention is directed to an intracorporeal device, preferably a guidewire, and method for making the same. The device, has proximal and distal ends and includes an elongated high strength proximal portion having proximal and distal ends. The device further includes a distal portion having proximal and distal ends. The distal end of the proximal portion and the proximal end of the distal portion are connected by a connector. The distal portion is formed of a superelastic alloy composition. Preferably, the connector is also formed of the superelastic alloy composition. The superelastic alloy composition includes, in atomic percent, from about 28 to about 52% nickel, from about 48 to about 52% titanium, and up to about 20% of least one alloying element selected from the group consisting of palladium, chromium, and hafnium, preferably, palladium.

When the alloying element is hafnium or palladium, the alloying element may be present, in atomic percent, in a range from about 3 to about 20%. Preferably, the hafnium or palladium may be present, in atomic percent, in a range from about 5 to about 11%.

When the alloying element is chromium, the alloying element is present, in atomic percent, in a range up to about 3%. Preferably, the chromium may be present, in atomic percent, in a range from about 0.1 to about 1%. More preferably, the chromium may be present, in atomic percent, in a range from about 0.2 to about 0.5%.

BRIEF DESCRIPTION OF THE DRAWINGS

FIG. 1 is an elevational view of a guidewire which embodies features of the invention.

FIG. 2 is a transverse cross sectional view of the guidewire of FIG. 1 taken along line 2—2.

FIG. 3 is a transverse cross sectional view of the guidewire of FIG. 1 taken along line 3—3.

DETAILED DESCRIPTION OF THE INVENTION

FIGS. 1, 2, and 3 illustrates a guidewire 10 embodying features of the invention that is adapted to be inserted into a patient's body lumen, such as an artery. The guidewire 10 comprises an elongated core 11 comprising a relatively high strength proximal portion 13, a relatively short distal portion 16 which is formed substantially of superelastic alloy material, and a connector element 19 which is formed substantially of superelastic alloy material and which connects a proximal end 22 of the distal portion 16 to a distal end 25 of the proximal portion 13 into a torque transmitting relationship. The distal portion 16 has at least one tapered section 28 which becomes smaller in the distal direction. The connector element 19 is a hollow tubular shaped element having an inner lumen 31 extending therein which is adapted to receive the proximal end 22 of the distal portion 16 and the distal end 25 of the proximal portion 13. The ends 22 and 25 may be press fit into the connector element 19 or they may be secured therein by crimping or swaging the connector or by means such as a suitable adhesive or by welding, brazing or soldering. The tubular connector 19 formed of superelastic alloy material provides a smooth transition between the high strength proximal portion 13 and the relatively short distal section 16 and retains a torque transmitting relationship between these two portions, 13 and 16.

A helical coil 34 is disposed about the distal portion 16 and has a rounded plug 37 on the distal end 40 thereof. The coil 34 is secured to the distal portion 16 at proximal location 43 and at intermediate location 46 by a suitable solder. A shaping ribbon 49 is secured by its proximal end 52 to the distal portion 16 at the same location 46 by the solder and by the distal end thereof 55 to the rounded plug 37 which is usually formed by soldering or welding the distal end of the coil 34 to the distal tip of the shaping ribbon 49. Preferably, the most distal section 58 of the helical coil 34 is made of radiopaque metal such as platinum, platinum-nickel, or iridium-tantalum alloys to facilitate the observation thereof by fluoroscopy while it is disposed within a patient's body. The most distal section 58 should be stretched about 10 to about 30%.

The most distal part 61 of the distal portion 16 is flattened into a rectangular section and preferably provided with a rounded tip 64, e.g. solder to prevent the passage of the most distal part 61 through the spacing between the stretched distal section 58 of the helical coil 34.

The exposed portion of the elongated proximal portion 13 should be provided with a coating 67 of lubricious material such as polytetrafluoroethylene (sold under the trademark Teflon® by du Pont, de Nemours & Co.) or other suitable lubricious coatings such as the polysiloxane coatings.

The elongated proximal portion 13 of the guidewire 10 is generally about 130 to about 140 cm in length with an outer diameter of about 0.006 to 0.018 inch for coronary use. Larger diameter guidewires may be employed in peripheral arteries and other body lumens. The lengths of the smaller diameter and tapered sections can range from about 2 to about 20 cm, depending upon the stiffness or flexibility desired in the final product. The helical coil 34 is about 20 to about 45 cm in length, has an outer diameter about the same size as the diameter of the elongated proximal portion 13, and is made from stainless steel wire about 0.002 to 0.003 inch in diameter. The shaping ribbon 49 and the flattened distal section 64 of distal portion 16 have rectangular transverse cross-sections which usually have dimensions of about 0.001 by 0.003 inch.

The hypotubing from which the connector 19 is formed generally may have an outer diameter from about 0.006 inch to about 0.02 inch with wall thicknesses of about 0.001 to about 0.004 inch. A presently preferred superelastic hypotubing for the connecting member 19 has an outer diameter of about 0.014 inch and a wall thickness of about 0.002 inch.

The superelastic members of the invention, i.e. the distal portion 16 and the connector 19, are preferably made of an alloy material composition including, by atomic percent, about 28 to about 52% nickel, preferably from about 34 to about 49% nickel; from about 48 to about 52% titanium; and up to about 20% of at least one alloying element selected from the group consisting of palladium, chromium, and hafnium. When the alloying element is palladium or hafnium, the alloying element is preferably present in a range from about 3 to about 20%, more preferably, from about 5 to about 11%. When the alloying element is chromium, the alloying element is preferably present up to about 3%, more preferably, from about 0.1 to about 1%, and most preferably from about 0.2 to about 0.5%. Preferably, the alloying element is palladium. Of course, the alloy material composition may include further elements for improving other desirable features such as manufacturability. The alloy material of the present invention has an increased ultimate tensile strength and tensile yield strength. This increase in the ultimate tensile strength and tensile yield strength provides for a guidewire having at least substantially the superelasticity and kink resistance of a guidewire made of NITINOL and substantially the increased modulus of elasticity and tensile strength of a guidewire made of stainless steel.

A presently preferred method for making the final configuration of the superelastic portions of the guiding member is to cold work, preferably by drawing, a rod or tubular member having a composition according to the relative proportions described above and then heat treating the cold worked product while it is under stress to impart a shape memory thereto. Typical initial transverse dimensions of the rod or the tubular member are about 0.045 inch and about 0.25 inch respectively. If the final product is to be tubular, a small diameter ingot, e.g. 0.25 to about 1.5 inch in diameter and 5 to about 30 inches in length, may be formed into a hollow tube by extruding or by machining a longitudinal center hole therethrough and grinding the outer surface thereof smooth. Before drawing the solid rod or tubular member, it is preferably annealed at a temperature of about 500° to about 750° C., typically about 650° C., for about 30 minutes in a protective atmosphere such as argon to relieve essentially all internal stresses. In this manner all of the specimens start the subsequent thermomechanical processing in essentially the same metallurgical condition so that products with consistent final properties are obtained. Such treatment also provides the requisite ductility for effective cold working.

The stressed relieved stock is cold worked by drawing to effect a reduction in the cross sectional area thereof of about 30 to about 70%. The metal is drawn through one or more dies of appropriate inner diameter with a reduction per pass of about 10 to 50%. Other forms of cold working can be employed such as swaging.

Following cold work, the drawn wire or hollow tubular product is heat treated at a temperature between about 350° and about 600° C. for about 0.5 to about 60 minutes. Preferably, the drawn wire or hollow tubular product is simultaneously subjected to a longitudinal stress between about 5% and about 50%, preferably about 10% to about 30% of the tensile strength of the material (as measured at room temperature) in order to impart a straight "memory" to the metal and to ensure that any residual stresses therein are uniform. This memory imparting heat treatment also fixes the austenite-martensite transformation temperature for the cold worked metal. By developing a straight "memory" and maintaining uniform residual stresses in the superelastic material, there is little or no tendency for a guidewire made of this material to whip when it is torqued within a patient's blood vessel.

An alternate method for imparting a straight memory to the cold worked material includes mechanically straightening the wire or tube and then subjecting the straightened wire to a memory imparting heat treatment at a temperature of about 300° to about 450° C., preferably about 330° to about 400° C. The latter treatment provides substantially improved tensile properties, but it is not very effective on materials which have been cold worked above 55%, particularly above 60%. Materials produced in this manner exhibit stress-induced austenite to martensite phase transformation at very high levels of stress but the stress during the phase transformation is not nearly as constant as the previously discussed method. Conventional mechanical straightening means can be used such as subjecting the material to sufficient longitudinal stress to straighten it.

The high strength proximal portion 13 of the guidewire generally is stronger, i.e. higher ultimate tensile strength, than the superelastic distal portion 16. Suitable high strength materials include 304 stainless steel which is a conventional material in guidewire construction.

Alternatively, due to the higher ultimate tensile strength and higher yield point of the alloy material of the present invention other portions of the guidewire, previously formed from stainless steel, may also be formed from the alloy material of the present invention. For example, in another embodiment, in addition to the distal portion of the core, one or more of the proximal portion 13, the connector 19 and the flattened most distal part 61 of the distal portion 16 may be formed from the alloy material of the present invention.

In another embodiment, the entire guidewire core 11 may be formed of the alloy material of the present invention. In addition when the entire guidewire core 11 is formed of the present alloy material, the proximal portion 11 and distal portion 16 are integral with one another without the presence of the connector 19.

The present invention provides guidewires which have superelastic characteristics to facilitate the advancing thereof in a body lumen. The guiding members exhibit extensive, recoverable strain resulting from stress induced phase transformation of austenite to martensite at exceptionally high stress levels which greatly minimizes the risk of damage to arteries during the advancement therein.

While particular forms of the invention have been illustrated and described, it will be apparent that various modifications can be made without departing from the spirit and scope of the invention. Accordingly, it is not intended that the invention be limited, except as by the appended claims.

What is claimed is:

1. An intravascular guidewire having proximal and distal ends, comprising:
    an elongated high strength proximal portion having proximal and distal ends;
    a distal portion having proximal and distal ends, the distal portion formed of a superelastic alloy composition; and
    means for connecting the distal end of the proximal portion and the proximal end of the distal portion and formed at least in part of the superelastic alloy composition, the superelastic alloy composition including, in atomic percent, from about 28 to about 52% nickel, from about 48 to about 52% titanium, and up to 20% hafnium as alloying element.

2. The guidewire of claim 1 wherein hafnium is present, in atomic percent, in a range from about 3 to about 20.

3. The guidewire of claim 2 wherein hafnium is present, in atomic percent, in range from about 5 to about 11.

4. An intravascular guidewire having proximal and distal ends, comprising:
    an elongated high strength proximal portion having proximal and distal ends;
    a distal portion having proximal and distal ends, the distal portion formed of a superelastic alloy composition; and
    means for connecting the distal end of the proximal portion and the proximal end of the distal portion and formed at least in part of the superelastic alloy composition, the superelastic alloy composition including, in atomic percent, from about 28 to about 52% nickel, from about 48 to about 52% titanium, and from about 0.1 to about 1% chromium.

5. The guidewire of claim 4 wherein chromium is present, in atomic percent, in a range from about 0.2 to about 0.5.

6. An intravascular guidewire having proximal and distal ends, comprising:
    a proximal and a distal portion each having proximal and distal ends; and
    means for connecting the distal end of the proximal portion and the proximal end of the distal portion, the proximal portion, the distal portion, and the connecting means formed of an alloy composition including, in atomic percent, from about 28 to about 52% nickel, from about 48 to about 52% titanium, and up to about 20% of at least one alloying element selected from the group consisting of palladium, chromium, and hafnium.

7. The guidewire of claim 6 wherein the alloying element is hafnium or palladium, and is present, in atomic percent, in range from about 3 to about 20.

8. The guidewire of claim 7 wherein the alloying element is present, in atomic percent, in range from about 5 to about 11.

9. The guidewire of claim 7 wherein the alloying element is palladium.

10. The guidewire of claim 6 wherein the alloying element is chromium and is present, in atomic percent, in a range up to about 3.

11. The guidewire of claim 10 wherein the alloying element is present, in atomic percent, in a range from about 0.1 to about 1.

12. The guidewire of claim 11 wherein the alloying element is present, in atomic percent, in a range from about 0.2 to about 0.5.

13. An intravascular guidewire having proximal and distal ends, comprising:
    an elongated core having distal and proximal portions, the core proximal and distal portions, independently including, in atomic percent, from about 28 to about 52% nickel, from about 48 to about 52% titanium, and up to about 20% of at least one alloying element selected from the group consisting of palladium, chromium, and hafnium.

14. The guidewire of claim 13 wherein the alloying element is hafnium or palladium, and is present, in atomic percent, in range from about 3 to about 20.

15. The guidewire of claim 14 wherein the alloying element is present, in atomic percent, in range from about 5 to about 11.

16. The guidewire of claim 14 wherein the alloying element is palladium.

17. The guidewire of claim 13 wherein the alloying element is chromium and is present, in atomic percent, in a range up to about 3.

18. The guidewire of claim 17 wherein the alloying element is present, in atomic percent, in a range from about 0.1 to about 1.

19. The guidewire of claim 18 wherein the alloying element is present, in atomic percent, in a range from about 0.2 to about 0.5.

20. The guidewire of claim 1 wherein hafnium is present, in atomic percent, up to about 20.

21. An intravascular guidewire having proximal and distal ends, comprising:

an elongated high strength proximal portion having proximal and distal ends;

a distal portion having proximal and distal ends, the distal portion formed of a superelastic alloy composition; and means for connecting the distal end of the proximal portion and the proximal end of the distal portion and formed at least in part of the superelastic alloy composition, the superelastic alloy composition including, in atomic percent, from about 28 to about 52% nickel, from about 48 to about 52% titanium, and from about 5 to about 11% of at least one alloying element selected from the group consisting of palladium, and hafnium.

* * * * *

UNITED STATES PATENT AND TRADEMARK OFFICE
CERTIFICATE OF CORRECTION

PATENT NO. : 6,352,515 B1  
DATED : March 5, 2002  
INVENTOR(S) : David M. Anderson et al.

It is certified that error appears in the above-identified patent and that said Letters Patent is hereby corrected as shown below:

<u>Title page,</u>  
Item [56], References Cited, U.S. PATENT DOCUMENTS, add:
-- 5,354,623    10/1994    Hall  
   5,637,089     6/1997    Abrams, et al.  
   5,749,370     5/1998    Brooks, et al. --.

FOREIGN PATENT DOCUMENTS, add:  
--   EP  0 520 073    12/1992,  
     EP  0 550 258     7/1993,  
     EP  0 879 614    11/1998 --.

Signed and Sealed this

Twenty-fourth Day of December, 2002

JAMES E. ROGAN  
*Director of the United States Patent and Trademark Office*